(12) United States Patent
Peters et al.

(10) Patent No.: US 6,939,969 B2
(45) Date of Patent: Sep. 6, 2005

(54) TRI-AND BIDENTATE AMIDO LIGANDS PREPARED BY PALLADIUM⁰ COUPLING AND METALLATION THEREOF TO FORM METAL-AMIDO CATALYSTS

(75) Inventors: Jonas C. Peters, Pasadena, CA (US); Steven D. Brown, Pasadena, CA (US); Seth B. Harkins, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 246 days.

(21) Appl. No.: 10/116,732

(22) Filed: Apr. 2, 2002

(65) Prior Publication Data

US 2003/0032808 A1 Feb. 13, 2003

Related U.S. Application Data

(60) Provisional application No. 60/281,044, filed on Apr. 2, 2001.

(51) Int. Cl.$^7$ ............................................. C07D 215/38
(52) U.S. Cl. ......................... 546/171; 556/64; 556/136; 556/137; 556/138; 556/140
(58) Field of Search .......................... 546/171; 556/64; 556/136, 137, 138, 140

(56) References Cited

U.S. PATENT DOCUMENTS

| | | |
|---|---|---|
| 6,235,938 B1 | 5/2001 | Hartwig et al. |
| 6,355,746 B1 | 3/2002 | Tagge et al. |

FOREIGN PATENT DOCUMENTS

JP          2000-109462    *   4/2000

OTHER PUBLICATIONS

Registry No. 70730–63–1, 1978.*
Buu Hoi et al, J. of the Chemical Society, abstract, 1956, 2048–2051.*
Chemical Reg No. 26866–32–0, 1970.*
Blache et al, Heterocycles, vol. 53, No. 4, pp 905–916, 2000.*
Dahl et al. (1969), "Studies of Chelates with Heterocyclic Ligands. IV. Transition Metal Complexes with N–(8–quinolyl)salicylaldimine," *Acta Chemica Scandinavica* 23(5):1503–1513.
Nieslen et al. (1966), "Studies of Chelates with Heterocyclic Ligands. II. Ionic Nickel(II) and Copper(II) Chelates with 8–aminoquinoline and Some of Its Derivatives," *Acta Chemica Scandinavica* 20(4):1113–1121.
Steiner et al. (1973), "Isomeriefälle bei Cr$^{III}$– und Co$^{III}$–1:2–Komplexen aus 8–(2'–Caroxyphenyl)–amino–chinolinen: Zur Frage der pyramidalen Struktur des koordinierten, dreibindigen Stickstoffatoms von Metallchelaten" ("Isomerism in Chromium(III) and Cobalt(III) 1:2 Complexes with 8–(2'–carboxyphenyl)aminoquinolines. Pyramidal Structure of the Coordinating, Trivalent Nitrogen Atom of Metal Chelates"), *Helvetica Chimica Acta* 56(1):368–374.
Jensen et al. (1964), "Studies of Chelates with Heterocyclic Ligands," *ACTA Chemica Scandinavica* 18(1):1–10.
Liu et al. (1999), "Dehydrogenation of n–Alkanes Catalyzed by Iridium 'Pincer' Complexes: Regioselective Formation of α–Olefins," *J. Am. Chem. Soc.* 121(16):4086–4087.
Peters et al. (2001), "Pincer–Like Amido Complexes of Platinum, Palladium, and Nickel," *Inorganic Chemistry* 40(20):5083–5091.
Puzas et al. (1986), "Direct Evidence for an $S_N1CB$ Mechanism. 4. Crystal and Molecular Structure of Chloro(bis(8–quinolinyl)amido–$N^1,N^2,N^3$)copper(II), a Metal Chelate Containing an sp$^2$–Hybridized Deprotonated Amine," *Inorganic Chemistry* 25(21):3837–3840.
Qian et al. (2000), "Synthesis and Structure of Li[C$_5$H$_4$)CH$_2$CH$_2$(TACN–'Pr$_2$)]. A Lithium Complex Supported by a Cp/TACN–$^i$Pr$_2$ Ligand," *Organometallics* 19(14):2805–2808.
Sundermann et al. (200), "Selective C–C vs C–H Bond Activation by Rhodium(I) PCP Pincer Complexes. A Computational Study," *J. Am. Chem. Soc.* 122(29):7095–7104.
Thomas et al. (2001), "Benzene C–H Activation at a Charge Neutral Zwitterionic Platinum(II) Complex," *J. Am. Chem. Soc.* 123(21):5100–5101.

* cited by examiner

*Primary Examiner*—Shailendra Kumar
(74) *Attorney, Agent, or Firm*—Reed Intellectual Property Law Group

(57) ABSTRACT

This invention provides an amido ligand and its synthesis. Use of the amide ligand in a variety of metal complexes, and transition metals in particular, is also provided.

31 Claims, No Drawings

TRI- AND BIDENTATE AMIDO LIGANDS PREPARED BY PALLADIUM⁰ COUPLING AND METALLATION THEREOF TO FORM METAL-AMIDO CATALYSTS

CROSS REFERENCE TO RELATED APPLICATIONS

This application claims priority under 35 U.S.C. §119(e)(1) to U.S. Provisional Application Ser. No. 60/281,044 filed on Apr. 2, 2001.

FIELD OF THE INVENTION

This invention relates to amido ligands, and 8-quinolinyl amine ligands in particular. The invention further relates to complexes formed between amido ligands and metals, such complexes finding utility in numerous catalytic applications.

BACKGROUND OF THE INVENTION

The study of late transition elements has gained increasing momentum in recent years because of their potential for catalyzing desirable transformations. A key feature of these metals is that they tend to be both more tolerant to functional groups and more robust toward air and moisture than other transition metals. In part because of these desirable properties, industrially important late metal polymerization catalysts are now under intense scrutiny. Furthermore, late transition metal systems are being studied for their ability to couple the activation and oxidation of light hydrocarbon substrates.

To build new molecular systems relevant to these and related goals, complexes supported by robust, anionic chelating ligands are being pursued. One type of anionic chelating ligand that has shown promise in the development of complexes with transition metal elements is the tridentate "pincer" type ligand. Rhodium (I) 1,3-bis[(di-tert-butylphosphino)methyl]-2,4,6-methylbenzine) (PCP) pincer complexes have been studied for use in selective C—C versus C—H bond activation (Sundermann et al. *J. Am Chem. Soc.* 122:7095–7104 (2000)). In addition, the use of iridium PCP pincer complexes in the regioselective formation of a-olefins has also been studied (Liu et al. *J. Am. Chem. Soc.* 121:4086–4087 (1999)).

The tridentate ligand bis(8-quinilinyl)amine (BQAH) and its derivatives are a family of ligands that afford rich reaction chemistry in the formation of transition metal complexes.

Methods for producing BQAH:

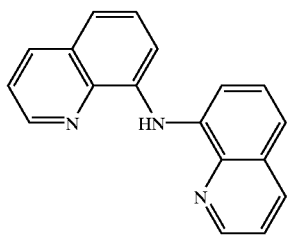

utilize a modified Bucherer reaction and take not only seven days for completion (Jensen et al. *Acta Chem. Scand.* 18:1–10 (1964)), but typically provide low yields of 4–8%. Therefore, there is a need for a faster and more efficient method for synthesizing these ligands.

The instant invention addresses that need by using a Pd⁰ catalyst in conjunction with a catalyst activator to quickly and efficiently synthesize BQAH and derivatives thereof with yields of greater than 80%.

SUMMARY OF THE INVENTION

One aspect of the invention pertains to a tri- or bidentate amido ligand having the formula (I):

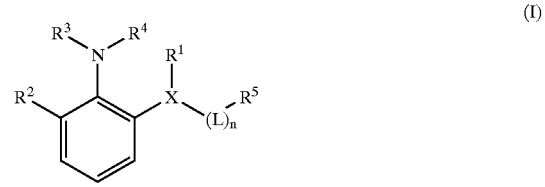

(I)

wherein: $R^1$ is selected from the group consisting of hydrogen, hydrocarbyl, substituted hydrocarbyl, heteroatom-containing hydrocarbyl and substituted heteroatom-containing hydrocarbyl; X is selected from the group consisting of N and P; L is hydrocarbylene; n is 0 or 1; $R^5$ is selected from the group consisting of hydrogen, hydrocarbyl, and substituted hydrocarbyl; and $R^2$, $R^3$, and $R^4$ are independently selected from the group consisting of hydrogen and hydrocarbyl, or $R^2$ and $R^3$ may be taken together to form a 5- or 6-membered ring structure selected from the group consisting of cycloalkyl, substituted cycloalkyl, aryl, substituted aryl, heteroaryl, and substituted heteroaryl; with the proviso that when $R^2$ and $R^3$ are taken together to form a 6-membered unsubstituted aryl ring, $R^1$ and $R^4$ are H, and n is 0, then $R^5$ may not be a quinoline moiety connected at the $C_8$ position.

Another aspect of the invention relates to a method for synthesizing compounds useful as amido ligands, comprising reacting (a) an amino-substituted, N-heteroaryl compound; and (b) a halogen-substituted aromatic compound in the presence of a transition metal catalyst.

Another aspect of the invention pertains to a complex having the formula (IV):

$$LM(Q)_r \quad (IV)$$

wherein: M is a metal; each Q is independently selected from the group consisting of hydrogen, halo, pseudo-halo, alkoxy, amido, $C_{1-15}$ hydrocarbyl, and substituted $C_{1-15}$ hydrocarbyl, or, if more than one Q moieties is present, the two or more Q moieties may be taken together to form a $C_{5-15}$ cycloalkyl group; r is 1, 2, or 3; and L is a ligand of formula (I).

Yet another aspect of the invention relates to the use of complexes of formula (IV) as catalysts.

DETAILED DESCRIPTION OF THE INVENTION

I. DEFINITIONS AND NOMENCLATURE

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a solvent" includes a single solvent as well as solvent mixture, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

"Alkenyl" as used herein refers to a linear, branched or cyclic hydrocarbon group of about 2–20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain about 2–12 carbon atoms. The term "lower alkenyl" intends an alkenyl group of about 2–6 carbon atoms, and the specific term "cycloalkenyl" intends a cyclic alkenyl group, preferably having about 5–8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

"Alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing about 1–6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

"Alkyl" as used herein refers to a linear, branched or cyclic saturated hydrocarbon group typically although not necessarily containing about 1–20 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain about 1–12 carbon atoms. The term "lower alkyl" intends an alkyl group of about 1–6 carbon atoms, and the specific term "cycloalkyl" intends a cyclic alkyl group, typically having about 4–8, preferably about 5–7, carbon atoms, and which is saturated or partially unsaturated (e.g., containing one or more double bonds). The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

"Alkylene" as used herein refers to a difunctional linear, branched or cyclic alkyl group, where "alkyl" is as defined above.

"Alkylsulfony" refers to the group —S(O)$_2$—R, where R is an alkyl group.

"Alkynyl" as used herein refers to a linear or branched hydrocarbon group of about 2–20 carbon atoms containing at least one triple bond, such as ethynyl, n-propynyl, and the like. Preferred alkynyl groups herein contain about 2–12 carbon atoms. The term "lower alkynyl" intends an alkynyl group of about 2–6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

"Amido" as used herein represents a group of the formula —C(O)NR'R" wherein R' and R" are independently selected from the group consisting of hydrogen, alkyl, cycloalkyl and alkenyl.

"Amino" is used herein to refer to the group —NR'R", where each of R' and R" is independently selected from the group consisting of hydrogen and optionally substituted alkyl, alkenyl, alkynyl, aryl, aralkyl, alkaryl and heterocyclic.

"Aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain one aromatic ring or 2–4 fused or linked aromatic rings, e.g., phenyl, naphthyl, biphenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom.

"Aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

"Halo" and "halogen" are used in the conventional sense to refer to a chloro, bromo, fluoro, or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

"Hydrocarbyl" refers to univalent hydrocarbyl radicals containing about 1–30 carbon atoms, preferably about 1–20 carbon atoms, most preferably about 1–15 and even more preferably about 1–12 carbon atoms, including linear, branched, cyclic, saturated and unsaturated species, such as alkyl groups, alkenyl groups, aryl groups, and the like. The term "lower hydrocarbyl" intends a hydrocarbyl group of about 1–6 carbon atoms, and the term "hydrocarbylene" intends a divalent hydrocarbyl moiety containing about 1–30 carbon atoms, preferably about 1–20 carbon atoms, most preferably about 1–12 carbon atoms, including linear, branched, cyclic, saturated and unsaturated species. The term "lower hydrocarbylene" intends a hydrocarbylene group of about 1–6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom.

"Pseudo-halo" refers to those compounds or substituents that behave as halides in their acid-base and redox chemistry. These include, by way of example, triflate (R—O—S(O)$_2$CF$_3$), acetates (R—O—C(O)CH$_3$), trifluoroacetate (R—O—C(O)CF$_3$), azide, cyanide and so forth.

"Substituted" as in "substituted hydrocarbyl," "substituted alkyl," "substituted aryl," and the like, as alluded to in some of the aforementioned definitions, is meant that in the hydrocarbyl, alkyl, aryl, or other moiety at least one hydrogen atom bound to a carbon atom is replaced with one or more non-hydrogen substituents, typically, although not necessarily, a functional group such as phosphonato, phosphoryl, phosphanyl, phosphino, sulfonato, alkylsulfanyl, arylsulfanyl, sulfonamido, amino, amido, imino, nitro, nitroso, hydroxyl, mercapto, formyl, haloformyl, thioester, acyl, cyano, isocyano, cyanato, isocyanato, thioisocyanato, carbamoyl, boryl, or the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

II. THE AMIDO LIGANDS

The invention pertains to tri- or bidentate amido ligands having the formula (I):

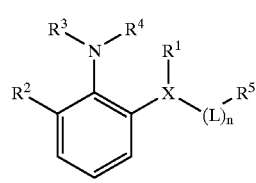

(I)

wherein:
R$^1$ is selected from the group consisting of hydrogen, hydrocarbyl, substituted hydrocarbyl, heteroatom-containing hydrocarbyl and substituted heteroatom-containing hydrocarbyl;
X is selected from the group consisting of N and P;
L is hydrocarbylene;
n is 0 or 1;
R$^5$ is selected from the group consisting of hydrogen, hydrocarbyl, substituted hydrocarbyl; and
R$^2$, R$^3$, and R$^4$ are independently selected from the group consisting of hydrogen and hydrocarbyl, or R$^2$ and R$^3$ may be taken together to form a 5- or 6-membered ring structure selected from the group consisting of cycloalkyl, substituted cycloalkyl, aryl, substituted aryl, heteroaryl, and substituted heteroaryl;

with the proviso that when R$^2$ and R$^3$ are taken together to form a 6-membered unsubstituted aryl ring, R$^1$ and R$^4$ are H, and n is 0, then R$^5$ may not be a quinoline moiety connected at the C$_8$ position.

In one embodiment of the invention, R$^1$ is selected from the group consisting of hydrogen, hydrocarbyl, substituted hydrocarbyl, more preferably hydrogen and alkyl, more preferably hydrogen and C$_{1-6}$ alkyl, and most preferably hydrogen.

Another preferred embodiment of the invention relates to those ligands of formula (I) where R$^2$ and R$^3$ are hydrogen or C$_{1-6}$ alkyl. In yet another embodiment, R$^2$ and R$^3$ are taken together to form a 5- or 6-membered ring structure, preferably an aryl, substituted aryl, heteroaryl, or substituted heteroaryl. In one preferred embodiment, R$^2$ and R$^3$ are taken together to form a 6-membered heteroaryl or substituted heteroaryl. Exemplary substituents on the heteroaryl include by way of example, and not limitation, alkyl, substituted alkyl, alkoxy, alkylsulfanyl, and amino. Preferred substituents include C$_{1-6}$ alkyl (e.g., methyl, ethyl, t-butyl, and so forth); C$_{1-6}$ alkoxy (methoxy, ethoxy, and so forth); C$_{1-6}$ alkylsulfanyl (e.g., methylsulfanyl, ethylsulfanyl and so forth); —NH$_2$; and C$_{1-6}$ alkyl substituted with amino groups (e.g. methylamino, dimethylamino, ethylamino, N-ethyl-N-methyl-amino, and so forth).

In one embodiment of the invention, R$^4$ is selected from the group consisting of hydrogen and alkyl, more preferably hydrogen and C$_{1-6}$ alkyl.

In another embodiment of the invention, n is 0 and thus L is absent so that X and R$^5$ are directly linked. In another embodiment, n is 1 and L acts as a hydrocarbylene linking group. A preferred hydrocarbylene linking group is a C$_{1-12}$ alkylene, more preferably C$_{1-6}$ alkylene, with methylene being most preferred.

In one preferred embodiment of the invention, R$^5$ is a hydrocarbyl or substituted hydrocarbyl, for example, an aryl, a substituted aryl, a heteroaryl or substituted heteroaryl group. Another preferred embodiment of the invention relates to those ligands of formula (I) where the R$^5$ group is phenyl, naphthyl, pyridinyl, or quinolyl, all of which can be optionally substituted with one or more moieties. Exemplary substituents include by way of example, and not limitation, alkyl, substituted alkyl, alkoxy, alkylsulfanyl, and amino. Preferred substituents include C$_{1-6}$ alkyl (e.g., methyl, ethyl, t-butyl, and so forth); C$_{1-6}$ alkoxy (methoxy, ethoxy, and so forth); C$_{1-6}$ alkylsulfanyl (e.g., methylsulfanyl, ethylsulfanyl and so forth); —NH$_2$; and C$_{1-6}$ alkyl substituted with amino groups (e.g. methylamino, dimethylamino, ethylamino, N-ethyl-N-methyl-amino, and so forth).

Examples of ligands of formula (I) include, by way of illustration and not limitation, the following compounds:

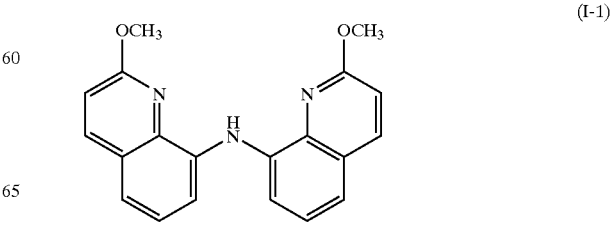

(I-1)

-continued (I-2) 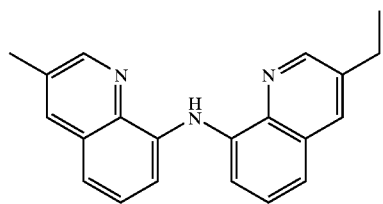

(I-3) 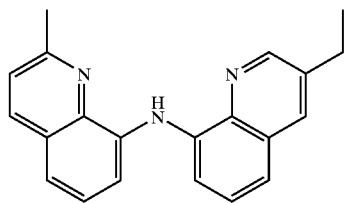

(I-4) 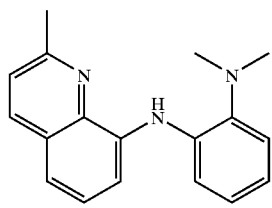

(I-5) 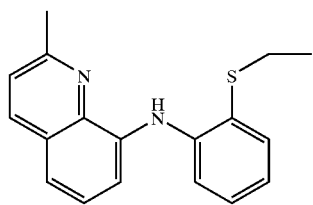

(I-6) 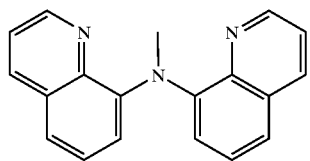

(I-7) 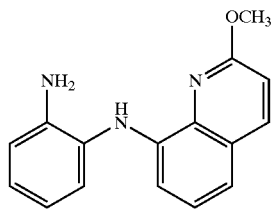

(I-8) 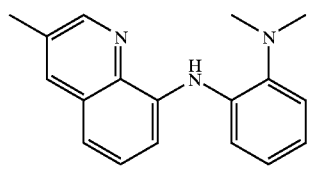

(I-9) 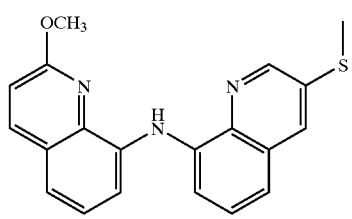

-continued (I-10) 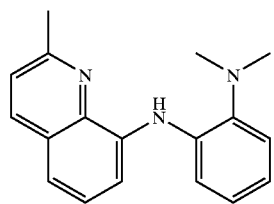

(I-11) 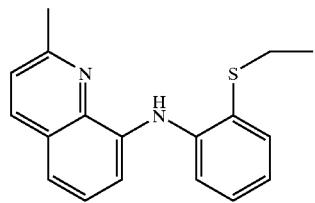

(I-12) 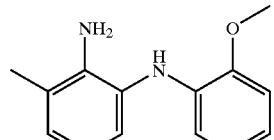

(I-13) 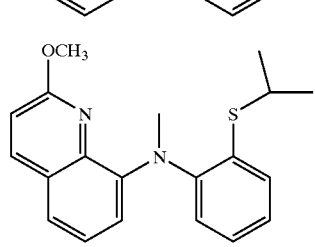

(I-14) 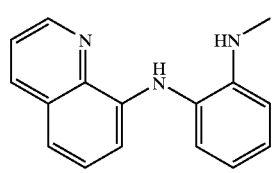

A preferred class of tri- or bidentate amido ligands have the formula (IA):

(IA) 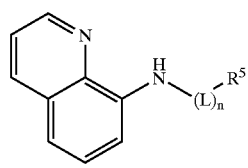

wherein:

L is hydrocarbylene;

n is 0 or 1; and $R^5$ is selected from the group consisting of hydrogen, hydrocarbyl, substituted hydrocarbyl;

with the proviso that when n is 0, then $R^5$ may not be a quinoline moiety connected at the $C_8$ position.

Examples of ligands of formula (IA) include, by way of illustration and not limitation, the tridentate compounds 2 and 3, and the bidentate compound 4 as shown in the Examples. In addition, compounds of formula (IA-1; q=1) and (IA-2) were synthesized with yields of 65% and 94% respectively:

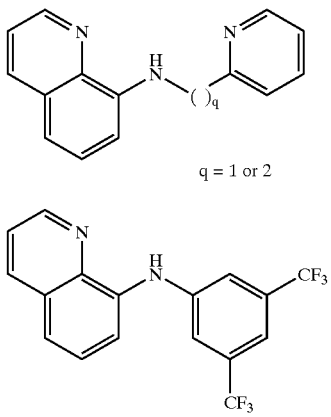

q = 1 or 2

III. LIGAND SYNTHESIS

The ligands of the invention are synthesized by reacting (a) an amino-substituted, N-heteroaryl compound and (b) a halogen-substituted aromatic compound in the presence of a transition metal catalyst, preferably a $Pd^0$-containing catalyst. In a preferred embodiment, the reaction is conducted in the presence of a base and under conditions effective to form the amido ligand.

A. LIGAND PRECURSORS

The amino-substituted, N-heteroaryl compound may have the structure of formula (II):

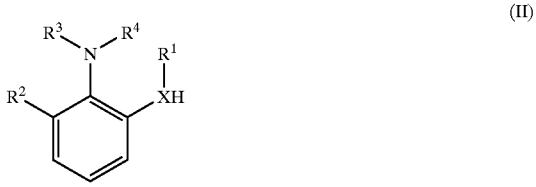

wherein:

$R^1$ is selected from the group consisting of hydrogen, hydrocarbyl, substituted hydrocarbyl, heteroatom-containing hydrocarbyl and substituted heteroatom-containing hydrocarbyl;

X is selected from the group consisting of N and P; and $R^2$, $R^3$, and $R^4$ are independently selected from the group consisting of hydrogen and hydrocarbyl, or $R^2$ and $R^3$ may be taken together to form a 5- or 6-membered ring structure selected from the group consisting of cycloalkyl, substituted cycloalkyl, aryl, substituted aryl, heteroaryl, and substituted heteroaryl.

In one embodiment of the invention, $R^2$ and $R^3$ are hydrogen, $C_{1-6}$ alkyl. In a preferred embodiment, $R^2$ and $R^3$ are taken together to form a 5- or 6-membered ring structure, preferably an aryl, substituted aryl, heteroaryl, or substituted heteroaryl. In a preferred embodiment, $R^2$ and $R^3$ are taken together to form a 6-membered heteroaryl or substituted heteroaryl.

Other preferred substituents are as described above for the compound of formula (I).

Exemplary amino-substituted, N-heteroaryl compounds include, by way of illustration and not limitation, 6-methyl-quinolin-8-ylamine, 6-methoxy-quinolin-8-ylamine, 1-(3-methyl-pyridin-2-yl)-ethylamine, and C-pyridin-2-yl-methylamine.

The a halogen substituted aromatic compound may have the structure of formula (III):

$$Z-(L)_n-R^5 \quad (III)$$

wherein:

Z is halo;

L is hydrocarbylene;

n is 0 or 1; and $R^5$ is selected from the group consisting of hydrogen, hydrocarbyl, and substituted hydrocarbyl.

In one embodiment of the invention, $R^5$ is a hydrocarbyl that contains two fused rings, which may be substituted. Exemplary substituents include by way of example, and not limitation, alkyl, substituted alkyl, alkoxy, alkylsulfanyl, and amino. Preferred substituents include $C_{1-6}$ alkyl (e.g., methyl, ethyl, t-butyl, and so forth); $C_{1-6}$ alkoxy (methoxy, ethoxy, and so forth); $C_{1-6}$ alkylsulfanyl (e.g., methylsulfanyl, ethylsulfanyl and so forth); $-NH_2$; and $C_{1-6}$ alkyl substituted with amino groups (e.g. methylamino, dimethylamino, ethylamino, N-ethyl-N-methyl-amino, and so forth).

Other preferred substituents are as described above for the compound of formula (I).

Exemplary halogen-substituted aromatic compounds include, by way of illustration and not limitation, 1-ethyl-3-fluoro-benzene, 8-fluoro-quinoline, chloro-benzene, 8-bromo-quinoline, (3-bromo-phenyl)-dimethyl-amine, and 1-bromo-3,5-dimethyl-benzene.

B. THE TRANSITION METAL CATALYST

The transition metal catalyst typically contains a metal and at least one chelating ligand. The metal is preferably a transition metal selected from the group consisting of metals from Group 8 (iron, ruthenium, osmium), Group 9 (cobalt, rhodium, iridium), and Group 10 (nickel, palladium, platinum) of the Periodic Table of the Elements. Particularly preferred transition metals include nickel, palladium, and platinum, and most preferably, palladium. These metals may exist in any oxidation state ranging from the zero-valent state to any higher variance available to the metal.

The chelating ligand may be a neutral molecule or charged ion. A chelating ligand possesses a plurality of coordination sites, typically two, three, or four. Preferably, the chelating ligand is a bidentate ligand, that is, one having two coordination sites. The chelating ligand also contains at least one metal atom from Group 15 (nitrogen, phosphorus, arsenic, antimony, bismuth) of the Periodic Table of the Elements, preferably, at least one element of nitrogen, phosphorus, or arsenic, and more preferably nitrogen or phosphorus. When only one of the Group 15 metals is present, then it is preferred to have at least a second chelating element, for example, oxygen or sulfur. Most preferably, the chelating ligand is selected from the group consisting of arylenes and metallocenes substituted with at least one metal atom from Group 15 ("Group 15-substituted arylenes" and "Group 15-substituted metallocenes").

The Term "Group 15-substituted arylenes" as used herein includes aromatic compounds substituted with at least one Group 15-containing moiety, preferably, at least one dialkyl or diaryl Group 15 moiety or hybrid thereof. The aromatic compound can be a single ring, fused ring, or multiple ring assembly. Other chelating elements, such as oxygen or sulfur, may be present. Non-limiting examples of Group 15-substituted arylenes which are chelating and beneficially employed in the process of this invention include 1,2-bis (diphenylphosphino) benzene, 2,2'-bis(diphenylphosphino)-1,1'-binaphthyl, 1-(dimethylarsino)-2-bis[(dimethylamino) phosphino]benzene, 1,2-bis(dimethylarsino)benzene, 5-10- dihydro-5,10-diphenyl-5-phospha-10-arsa-anthracene, 2-diphenylphosphino-N,N-dimethylaniline, 1,8-bis(diphenylphosphino) naphthalene, 2,2'-bis(diphenylphosphino)diphenyl ether, 4,5-bis(diphenylphosphino)-9,9-dimethyl)xanthene, and 2,2'-bis(di-p-tolylphosphino)-1,1'-binaphthyl, 1-diphenylphosphino-1'-dimethylamino-2,2'-binaphthyl, 1-dicyclohexylphosphino-1'-dimethylamino-2,2'-binaphthyl, 1-di-t-butylphosphino-1'-dimethylamino-2,2'-binaphthyl, 1-di-i-propylphosphino-1'-dimethylamino-2,2'-binaphthyl, 1-diphenylphosphino-1'-methoxy-2,2'-binaphthyl, 1-dicyclohexylphosphino-1'-methoxy-2,2'-binaphthyl, 1-di-t-butylphosphino-1'-methoxy-2,2'-binaphthyl, 1-di-i-propylphosphino-1'-dimethylamino-2,2'-binaphthyl, 1-diphenylphosphino-1'-dimethylamino-2,2'-biphenyl, 1-dicyclohexylphosphino-1'-dimethylamino-2,2'-biphenyl, 1-di-t-butylphosphino-1'-dimethylamino-2,2'-biphenyl, 1-di-i-propylphosphino-1'-dimethylamino-2,2'-binaphthyl, 1-diphenylphosphino-1'-methoxy-2,2'-biphenyl, 1-dicyclohexylphosphino-1'-methoxy-2,2'-biphenyl, 1-di-t-butylphosphino-1'-methoxy-2,2'-biphenyl, 1-di-i-propylphosphino-1'-dimethylamino-2,2'-binaphthyl, 2-di-t-butylphosphinophenylethyl-di-t-butylphosphine, and 2-di-t-butylphosphinobenzyl-di-t-butylphosphine Analogous diamino, diphosphino, and diarsino compounds and hybrids thereof are also suitable. Preferably, the Group 15-substituted arylene is a Group 15-substituted $C_{4-20}$ arylene, more preferably, a Group 15-substituted binaphthyl compound, more preferably, 2,2'-bis(diphenylphosphino)-1,1'-binaphthyl (BINAP) or 2,2'-bis(di-p-tolyl-phosphino)-1,1'-binaphthyl.

The term "Group 15-substituted metallocenes" as used herein includes metallocenes that are substituted with at least one Group 15-containing moiety, preferably at least one dialkyl or diaryl Group 15 moiety or hybrid thereof. Other chelating elements, for example, oxygen or sulfur, may be present. The metallocene itself comprises a transition metal atom or ion which is bonded to one or more $C_{4-8}$ multiply unsaturated hydrocarbon ring compounds. Suitable non-limiting examples of transition metal atoms in the metallocene include iron, titanium, vanadium, chromium, manganese, cobalt, nickel, molybdenum, and ruthenium. Preferably, the transition metal atom in the metallocene is iron. The $C_{4-8}$ multiple unsaturated hydrocarbon ring compounds suitably include cyclobutadiene, cyclopentadienyl, benzene, cycloheptatrienyl, and cyclooctatetraene. Representative metallocenes include ferrocene, ruthenocene, bis(benzene)chromium, bis(benzene)molybdenum, bis(benzene)tungsten, and cobaltocenium. Non-limiting examples of ligands which classify as chelating Group 15-substituted metallocenes include 1,1'bis(diphenylphosphino)ferrocene, 1-diphenylphosphino-2-(1-dimethylamino)ethyl ferrocene, 1-diphenylarsino-1'-diphenyl-phosphino ferrocene, 1-diphenylphosphino-2-(1-diphenylphosphino)ethyl ferrocene, 1-diphenylphosphino-2-(1-di-t-butylphosphino)ethyl ferrocene, 1-diphenylphosphino-2-(1-dicyclohexylphosphino)ethyl ferrocene, 1-dicyclohexyl phosphino-2-(1-diphenylphosphino)ethyl ferrocene, 1-dicyclohexylphosphino-2-(1-dicyclohexylphosphino) ethyl ferrocene, 1-dicyclohexylphosphino-2-(1-dimethylamino)ethyl ferrocene, 1-di-t-butylphosphino-2-(1-dimethylamino)ethyl ferrocene, 1-di-i-propylphosphino-2-(1-dimethylamino)ethyl ferrocene, 1-diphenylphosphino-2-(1-dimethylamino)ethyl ferrocene, 1-[2-(diphenylphosphino)ferrocenyl]ethyl methyl ether, 1-[2-(dicyclohexylphosphino)ferrocenyl]ethyl methyl ether, 1-[2-(di-i-propylphosphino)ferrocenyl]ethyl methyl ether, 1-[2-(di-t-butylphosphino)ferrocenyl]ethyl methyl ether, (-)-(R)-N,N-dimethyl-1-[(S)-1',2-bis(diphenylphosphino)ferrocenyl]ethylamine, (+)-(S)-1-[(R)-2-(diphenylphosphino)ferrocenyl]ethyl methyl ether, and N,N-dimethyl-1,2-bis(di-t-butylphosphino)ferrocenyl]ethylamine. Analogous phosphine and amine substituted derivatives of the aforementioned metallocenes may also be employed. Preferably, the Group 15-substituted metallocene is a Group 15-substituted ferrocene, more preferably, 1,1'-bis(diphenylphosphino)ferrocene (DPPF).

In one preferred embodiment, the chelating ligand is a bidentate ligand containing at least one phosphorous atom. More preferably, the chelating ligand is a bidentate ligand selected from the group consisting of phosphorous-substituted arylenes and phosphorous-substituted metallocenes. Most preferably, the ligand is 2,2'-bis(diphenylphosphino)-1,1'-binapthyl (BINAP), 1,1'-bis(di-p-tolylphosphino)-2,2'-binapthyl(Tol-BINAP), or 1,1'-bis(diphenyl phosphino)ferrocene (DPPF).

Methods for preparing the aforementioned catalysts are known to those skilled in the art. For a description of general synthetic techniques, see Inorganic Synthesis: Reagents for Transition Metal Complex and Organometallic Systems; R. J. Angelici, Ed., Wiley-Interscience: New York, 1990, Vol. 28, pp. 77–135 (Chapter 2), incorporated herein by reference, wherein representative preparations of Group 8 complexes containing chelating amine, phosphine, and arsine ligands are taught.

The transition metal catalyst may be synthesized first and thereafter employed in the arylation process. Alternatively, the catalyst can be prepared in situ in the ligand reaction mixture. If the latter mixture is employed, then a transition metal catalyst precursor compound and the desired chelating ligand are independently added to the reaction mixture wherein formation of the transition metal catalyst occurs in situ. Suitable precursor compounds include alkene and diene complexes of the transition metals (Groups 8, 9 and 10), preferably, di(benzylidene)acetone (dba) complexes of the Group 8 metals, as well as, monodentate phosphine complexes of the Group 8 metals, and Group 8 carboxylates. In the presence of the chelating ligand, such as DPPF or BINAP, in situ formation of the transition metal catalyst occurs. Non-limiting examples of suitable precursor compounds include [bis-di(benzylidene)acetone]palladium (0), tetrakis-(triphenylphosphine)-palladium (0), tris-[di(benzylidene)acetone]palladium (0), tris-[di(benzylidene)acetone]-dipalladium (0) ($Pd_2(dba)_3$), palladium acetate, and the analogous complexes of iron, cobalt, nickel, ruthenium, rhodium, osmium, iridium, and platinum. Any of the aforementioned catalyst precursors may include a solvent of crystallization. Group 8 metals supported on carbon, preferably, palladium on carbon, can also be suitably employed as a precursor compound. Preferably, the catalyst precursor compound is $Pd_2(dba)_3$.

The quantity of transition metal catalyst which is employed in the methods of this invention is any quantity which promotes the formation of the amido ligand. Generally, the quantity is a catalytic amount, which means that the catalyst is used in an amount which is less than stoichiometric relative to precursors of the amido ligand. Typically, the transition metal catalyst ranges from about 0.01–20 mole percent, based on the number of moles of the compound having at least one unsaturated nitrogen atom used in the reaction. Preferably, the quantity of transition metal catalyst ranges from about 1–10 mole percent, and more preferably from about 3 to about 8 mole percent, based on the moles of the unsaturated nitrogen-containing compound.

C. THE BASE

Any base may be used so long as the method of the invention proceeds to the amido ligand product. Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethyl-ammonium hydroxide and tetraethylammonium hydroxide; and diaza organic bases, such as 1,8-diazabicyclo[5.4.0]-undec-7-ene and 1,8-diazabicyclo-[2.2.2.]-octane. Preferably, the base is an alkali hydroxide or alkali alkoxide, more preferably, an alkali alkoxide, and most preferably, an alkali metal $C_{1-10}$ alkoxide such as NaOtBu.

The quantity of base which is used can be any quantity which allows for the formation of the amido ligand. Preferably, the molar ratio of base to the ligand precursors ranges from about 1:1 to about 3:1, and more preferably between about 1:1 and 2:1.

D. METHOD OF SYNTHESIS

Generally, the ligand precursors, transition metal catalyst, and base may be mixed together or added to a solvent in any order. Any solvent can be used in the process of the invention provided that it does not interfere with the formation of the amido ligand product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as tetrahydrofuran. Suitable protic solvents include, but are not limited to, water and aliphatic alcohols, such as ethanol, isopropanol, and cyclohexonol, as well as glycols and other polyols. The amount of solvent which is employed may be any amount, preferably an amount sufficient to solubilize, at least in part, the reactants and base. A suitable quantity of solvent typically ranges from about 1–100 grams solvent per gram reactants. Other quantities of solvent may also be suitable, as determined by the specific process conditions and by the skilled artisan.

Air is preferably removed from the reaction vessel during the course of the reaction, however this step is not always necessary. If it is desirable or necessary to remove air, the solvent and reaction mixture can be purged with a non-reactive gas, such as nitrogen, helium, or argon, or the reaction may be conducted under anaerobic conditions. The process conditions can be any operable conditions that yield the desired ligand product. Preferably the reaction is held at a temperature ranging from about 20–150° C., preferable from about 75–120° C. The process may be run at atmospheric pressure or sub-atmospheric pressures if necessary. Typical reaction times range from about 30 minutes to about 5 days, reaction times on the order of about 2–3 days are more common.

The resulting transition metal amido ligand can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of ligand product recovered, based on the number of moles of the amino-substituted aromatic nitrogen heterocyclic precursor employed. Typically, the yield of ligand product is greater than about 50 mole percent. Preferably, the yield of ligand product is greater than about 60 mole percent, and more preferably, greater than about 80 mole percent.

IV. METAL AMIDO LIGAND COMPLEXES

In another embodiment of the invention, the tri- or bidentate amido ligands of formula (I) are used to form complexes with metals, and particularly transition metals. In general, the complexes may be prepared using standard metallation procedures which are relatively simple and straightforward synthetic processes known to those skilled in the art and/or described in the pertinent texts and literature.

Two preferred methods of installing the amido ligands on to metals are (i) transmetallation using an alkali ligand precursor and (ii) dehydrohalogenation using the ligand in the presence of base. For example, reaction of BQAH/NEt$_3$ with cyclooctadiene PtCl$_2$ in methylene chloride solution generates (BQA)PtCl quantitatively with concomitant liberation of cyclooctadiene. Removal of the hydrochloride salt byproduct may be accomplished either by ethanol washing of the alcohol insoluble product or by extracting the target complex with benzene and filtering it away from Et$_3$NaHCl. Alternatively, a ligand/metal complex can be prepared by transmetalation with [Li][BQA] in benzene at 65° C. Suitable metallation reactions are described in Examples 7–14. Other suitable metallation reactions for preparing the present compounds will be known to those skilled in the art and/or described in or readily derived from the pertinent texts and literature.

The resulting amido ligand metal complexes have the formula (IV):

wherein:

M is a metal;

each Q is independently selected from the group consisting of hydrogen, halo, pseudo-halo, alkyl, alkoxy, amido, $C_{1-15}$ hydrocarbyl, and substituted $C_{1-15}$ hydrocarbyl, or, if more than one Q moieties is present, the two or more Q moieties may be taken together to form a $C_{5-15}$ cycloalkyl;

r is 1, 2, or 3; and

L is a ligand having the formula:

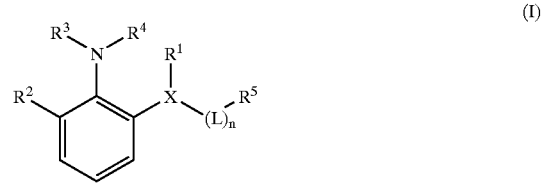

wherein:

$R^1$ is selected from the group consisting of hydrogen, hydrocarbyl, substituted hydrocarbyl, heteroatom-containing hydrocarbyl and substituted heteroatom-containing hydrocarbyl;

X is selected from the group consisting of N and P;

L is hydrocarbylene;

n is 0 or 1;

$R^5$ is selected from the group consisting of hydrogen, hydrocarbyl, substituted hydrocarbyl; and $R^2$, $R^3$, and $R^4$ are independently selected from the group consisting of hydrogen and hydrocarbyl, or $R^2$ and $R^3$ may be taken together to form a 5- or 6-membered ring structure selected from the group consisting of cycloalkyl, substituted cycloalkyl, aryl, substituted aryl, heteroaryl, and substituted heteroaryl;

with the proviso that when $R^2$ and $R^3$ are taken together to form a 6-membered unsubstituted aryl ring, $R^1$ and $R^4$ are H, and n is 0, then $R^5$ may not be a quinoline moiety connected at the $C_8$ position.

M can be any suitable metal such as zinc; thallium; metals from Group 3 (scandium, yttrium, lanthanum, actinium), Group 4 (titanium, zirconium, hafnium), Group 5 (vanadium, niobium, tantalum), Group 6 (chromium, molybdenum, tungsten), Group 7 (manganese, technetium, rhenium), Group 8 (iron, ruthenium, osmium), Group 9 (cobalt, rhodium, iridium), Group 10 (nickel, palladium, platinum), and Group 11 of the Periodic Table of the Elements; the lanthanides (cerium, praseodymium, neodymium, promethium, samarium, europium, gadolinium, terbium, dysprosium, holmium, erbium, thulium, ytterbium, and lutetium); and the actinides (thorium, protactinium, uranium, neptunium, plutonium, americium, curium, berkelium, californium, einsteinium, fermium, mendelevium, nobelium, and lawrencium.).

In a preferred embodiment, M is a metal selected from the group consisting of zirconium, manganese, zinc, thallium, thorium, uranium, and transition metals from Group 8, Group 9, and Group 10 of the Periodic Table of the Elements. Particularly preferred transition metals include nickel, palladium, and platinum.

Examples of amido ligand transition metal complexes of formula (IV) include, by way of illustration and not limitation, compounds 7, 8, and 9 as shown in the Examples.

In another preferred embodiment, Q is preferably halo, pseudo-halo, or alkyl.

The amido ligand transition metal complexes of the invention are expected to find utility as catalysts in numerous stoichiometric and catalytic transformations such as, by way of example and not limitation, hydroamination, olefin hydration, alkane oxidation, dioxygen activation and subsequent olefin epoxidation, dinitrogen activation/reduction/functionalization, olefin polymerization/copolymerization/living polymerization, catalytic C-E bond formation (where E is C, N, O, S, Si, H, and so forth), as well as Heck, Suzuki and Sonagoshira coupling reactions (preferably with the metal being nickel or palladium)

All patents, publications, and other published documents mentioned or referred to in this specification are herein incorporated by reference in their entirety.

It is to be understood that while the invention has been described in conjunction with the preferred specific embodiments hereof, the foregoing description, as well as the examples which are intended to illustrate and not limit the scope of the invention, it should be understood by those skilled in the art that various changes may be made and equivalents may be substituted without departing from the scope of the invention. Other aspects, advantages and modifications will be apparent to those skilled in the art to which the invention pertains.

EXAMPLES

The practice of the present invention will employ, unless otherwise indicated, conventional techniques of pharmaceutical formulation, medicinal chemistry, and the like, which are within the skill of the art. Such techniques are explained fully in the literature.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. All components were obtained commercially unless otherwise indicated.

In describing and claiming the present invention, the following abbreviations will be used in accordance with the definitions set out below.

| ABBREVIATIONS | |
|---|---|
| BQAH | bis(8-quinilinyl)amine |
| COD | cyclooctadiene |
| dba | di(benzylidene)acetone |
| DCM | dichloromethane |
| DME | 1,2-dimethoxyethane |
| DPPF | 1,1'-bis(diphenylphosphino)ferrocene |
| Et | ethyl |
| Et$_2$O | diethyl ether |
| Et$_3$N | triethylamine |
| EtOH | ethanol |
| Me | methyl |
| NaOtBu | sodium-t-butoxide |
| Ph | phenyl |
| rac-BINAP | rac-2,2'-bis(diphenylphosphino)-1,1'binaphthyl |
| RT | room temperature |
| THF | tetrahydrofuran |

MATERIALS AND METHODS

All manipulations were carried out using standard Schlenk or glovebox techniques under a dinitrogen atmosphere. Unless otherwise noted, solvents were deoxygenated and dried by thorough sparging with gas followed by passage through an activated alumina column. Nonhalogenated solvents were typically tested with a standard purple solution of sodium benzophenone ketyl in THF to confirm effective oxygen and moisture removal. The reagent 8-bromoquinoline was synthesized according to the method disclosed by Butler et al., *J. Heterocycl. Chem.* 12:1015–1020 (1975). 2-Bromo-N,N-dimethylaniline was prepared as described in Kelly et al., *Aust. J. Chem.* 47:1751–1769 (1994). The preparation of ($\eta^2$, $\eta^2$-cycloocta-1,5-diene) PdCl$_2$,((COD)PdCl$_2$) and (COD)PtMeCl were carried out as described in Chatt et al., *J. Chem. Soc.* 3413–3416 (1957). (COD)PdMeCl was prepared as described in Ike et al., *Inorg. Chem.* 32:5769–5778 (1993). (DME)NiCl$_2$ was prepared as described in Ward *Inorg. Synth.* 13:154 (1971). (COD)PtCl$_2$ was prepared as described in Clark et al., *J. Organomet. Chem* 59:411–428 (1973). Other reagents were purchased from commercial vendors and used without further purification. Elemental analyses were performed by Desert Analytics, Tucson, Ariz. A Varian Mercury-300 NMR spectrometer or a Varian Inova-500 NMR spectrometer was used to record $^1$H and $^{13}$C NMR spectra unless otherwise stated. $^1$H and $^{13}$C NMR chemical shifts were referenced to residual solvent. MS data for samples were obtained by injection of an acetonitrile solution into a Hewlett-Packard 1100MSD mass spectrometer (ES$^+$) or an Agilent 5973 mass selective detector (EI). Deuterated chloroform and benzene were degassed and dried over activated 3 Å molecular sieves prior to use.

Example 1

Synthesis of BQAH (1)

A 200 mL reaction vessel equipped with a Teflon stopcock and stir bar was charged with Pd$_2$(dba)$_3$ (0.176 g, 0.192 mmol), rac-BINAP (0.239 g, 0.384 mmol), and toluene (30 mL) under a dinitrogen atmosphere. The resulting solution was allowed to stir for 5 min, after which time 8-bromoquinoline (2.00 g, 9.61 mmol), 8-aminoquinoline (1.39 g, 9.64 mmol), and additional toluene (70 mL) were added. The subsequent addition of NaOtBu (1.11 g, 11.5 mmol) resulted in a red solution that was stirred vigorously for 36 hours at 110° C. The solution was then allowed to cool and filtered through a silica plug that was then extracted with DCM to ensure complete removal of the desired product. Concentration of the collected extracts and removal of solvent yielded a crude red solid (2.37 g, 91%). Purification by flash chromatography on silica gel (4:1 toluene/ethyl acetate) yielded orange, solid bis(8-quinolinyl)amine (1.95 g, 75%) as a spectroscopically pure and synthetically useful compound. Characterization data for (1) compared favorably with that previously reported.

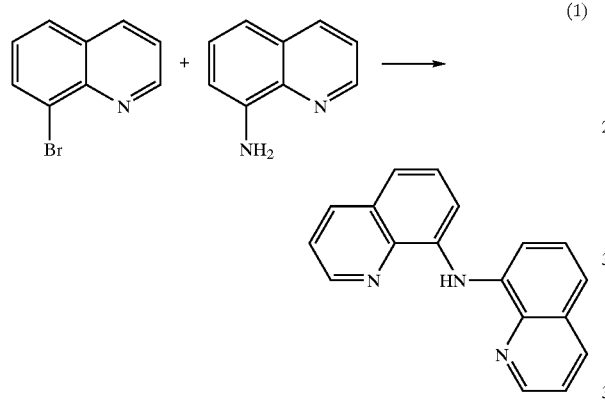

(1)

$^1$H NMR (CDCl$_3$, 300 MHz, 25° C.): δ 10.65 (s, 1H), 8.97 (dd, J=1.7, 2.2 Hz, 2H), 8.16 (dd, J=1.7, 8.3 Hz, 2H), 7.92 (d, J=6.5 Hz, 2H), 7.58–7.42 (m, 4H), 7.34 (d, J=7 Hz, 2H). $^{13}$C NMR (CDCl$_3$, 75 MHz, 25° C.): δ 148.1, 140.1, 138.8, 136.2, 129.1, 127.2, 121.7, 117.9, 110.1. LR-MS (electrospray): calculated for C$_{17}$H$_{17}$N$_3$ (M)$^+$ m/z 271. found (M+H)$^+$ m/z 272.

Example 2

Synthesis of 2-Pyridin-2-yl-ethyl-QAH (2)

A 200 mL reaction vessel with a stir bar was charged with Pd$_2$(dba)$_3$ (0.170 g, 0.186 mmol), rac-BINAP (0.232 g, 0.372 mmol), and toluene (20 mL) under a dinitrogen atmosphere. The resulting solution was allowed to stir for 5 min, after which time 8-bromoquinoline (1.549 g, 7.45 mmol), 2-(2-aminoethyl)pyridine (1.000 g, 8.19 mmol), and additional toluene (20 mL) were added. The subsequent addition of NaOtBu (1.002 g, 10.43 mmol) caused the reaction slurry to turn red, and the contents were stirred vigorously for 18 h at 90° C. The final purple solution was cooled to ambient temperature, and the solvent was removed in vacuo affording a viscous violet liquid. Purification by flash chromatography on silica gel (1:1 toluene/ethyl acetate) yielded a red oil that was extracted with Et$_2$O, filtered, and dried under vacuum for 24 h to yield the desired product (1.584 g, 85%).

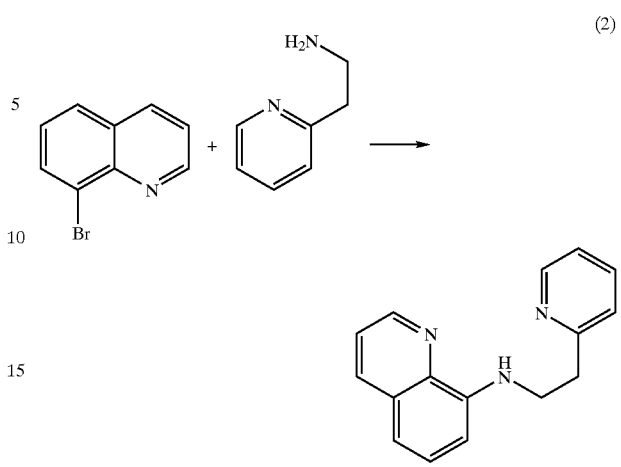

(2)

$^1$H NMR (CDCl$_3$, 500 MHz, 25° C.): δ 8.60 (dd, J=4.2, 1.5 Hz, 1H), 8.51 (d, J=3.9 Hz, 1H), 7.94 (dd, J=8.1, 2.0 Hz, 1H), 7.49 (m, 1H), 7.30 (m, 1H), 7.25 (m, 1H), 7.0–7.12 (m, 2H), 6.95 (dd, J=8.1, 1.5 Hz, 1H), 6.66 (d, J=6.9 Hz, 1H), 6.31 (br s, NH), 3.66 (m, 2H), 3.15 (t, J=7 Hz, 2H). $^{13}$C NMR (CDCl$_3$, 75 MHz, 25° C.): δ 159.8, 149.7, 147.0, 144.8, 138.4, 136.6, 136.1, 128.9, 128.0, 123.6, 121.6, 121.5, 114.0, 104.9, 43.4, 37.9. GC-MS (EI): calculated for C$_{16}$H$_{15}$N$_3$ (M)$^+$ m/z 249. found (M)$^+$ m/z 249.

Example 3

Synthesis of o-(NMe$_2$)Ph-QAH (3)

A 200 mL reaction vessel equipped with a Teflon stopcock and stir bar was charged with Pd$_2$(dba)$_3$ (0.915 g, 0.999 mmol), DPPF (1.11 g, 2.00 mmol), and toluene (100 mL) under a dinitrogen atmosphere. The resulting solution was allowed to stir for 5 min, after which time 8-aminoquinoline (3.60 g, 0.0250 mol), N,N-dimethyl-o-bromoaniline (5.00 g, 0.025 mol), and NaOtBu (2.88 g, 0.030 mol) were added. This solution was stirred vigorously for 3 days at 110° C. after which time it was cooled to RT and filtered through a silica plug. Ethyl acetate was used to elute the plug to ensure complete removal of the desired product. Removal of volatiles in vacuo yielded a crude red liquid. The remaining starting materials were removed via vacuum distillation, and the resulting liquid was filtered once more through a silica gel plug. The orange residue obtained after drying in vacuo (3.56 g, 54%) solidified upon standing at RT for 5 days.

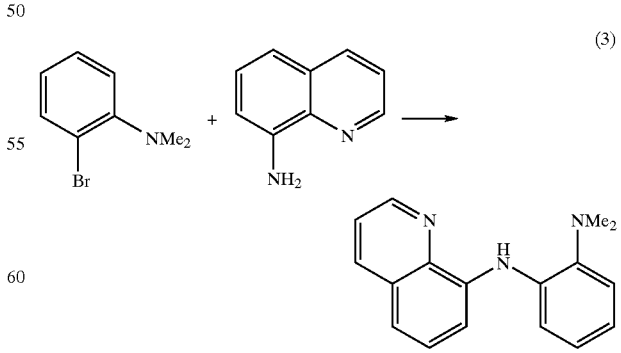

(3)

$^1$H NMR (CDCl$_3$, 300 MHz, 25° C.): δ 8.85 (dd, J=1.8, 4.2 Hz, 1H), 8.71 (s, 1H), 8.13 (dd, J=1.5, 8.1 Hz, 1H), 7.67 (dd, J=1.8, 8.1 Hz, 1H), 7.60 (dd, J=1.2, 7.8 Hz, 1H), 7.45

(dd, J=1.5, 6.0 Hz, 1H), 7.43 (m, 1H), 7.24–6.97 (m, 5H), 2.75 (s, 6H). $^{13}$C NMR (CDCl$_3$, 75 MHz, 25° C.): δ 147.6, 145.1, 140.0, 139.3, 136.1, 136.0, 129.1, 127.4, 123.2, 121.6, 119.4, 117.8, 116.4, 107.8, 44.1. LR-MS (electrospray): calculated for C$_{17}$H$_{17}$N$_3$ (M)$^+$ m/z 263. found (M+H)$^+$ m/z 264.

Example 4

Synthesis of 3,5-Me$_2$Ph-QAH (4)

A 200 mL reaction vessel equipped with a Teflon stopcock and stir bar was charged with Pd$_2$(dba)$_3$ (0.222 g, 0.242 mmol), DPPF (0.268 g, 0.483 mmol), and 20 mL of toluene under a dinitrogen atmosphere. The resulting solution was allowed to stir for 5 min, after which time 8-aminoquinoline (0.873 g, 6.05 mmol), 3,5-dimethyl-bromobenzene (1.12 g, 6.05 mmol), and NaOtBu (1.16 g, 12.1 mmol) were added. The solution was allowed to stir at 110° C. for 24 h, after which time it was allowed to cool and filtered over silica gel. Toluene was then removed in vacuo, and flash chromatography on silica gel (115:1 toluene/ethyl acetate) yielded spectroscopically pure 4 as an orange liquid (1.28 g, 85%).

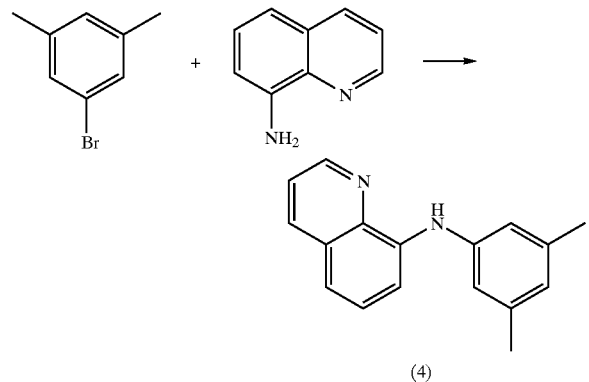

(4)

$^1$H NMR (CDCl$_3$, 300 MHz, 25° C.): δ 8.79 (dd, J=1.5, 4.2 Hz, 1H), 8.21 (s, 1H), 8.12 (dd, J=1.8, 8.4 Hz, 1H), 7.52–7.20 (m, 4H), 7.05 (s, 2H), 6.72 (s, 1H), 2.40 (s, 6H). $^{13}$C NMR (CDCl$_3$, 75 MHz, 25° C.): δ 147.3, 141.8, 140.5, 139.1, 138.3, 136.3, 129.0, 128.5, 124.1, 121.7, 118.0, 116.3, 108.0, 21.8. LR-MS (electrospray): calculated for C$_{17}$H$_{16}$N$_2$ (M)$^+$ m/z 248. found (M+H)$^+$ m/z 249.

Example 5

Synthesis of [Li][BQA] (5)

A solution of 1.6 M n-butyllithium in hexanes (4.82 mL, 7.71 mmol) diluted with toluene (20 mL) was added dropwise over 30 min to a stirring solution of BQAH (2.089 g, 7.71 mmol) in toluene (250 mL) at −78° C. The reaction mixture was then allowed to warm slowly to RT. After the reaction mixture was stirred for an additional 24 h, the solvent was removed in vacuo, affording a bright orange solid. The product was lyophilized from 50 mL of benzene, washed with petroleum ether (3×30 mL), and dried in vacuo affording spectroscopically pure 5 (1.880 g, 88%).

$^1$H NMR (CDCl$_3$, 300 MHz, 25° C.): δ 7.84 (d, J=7.7 Hz, 2H), 7.70 (d, J=8.2 Hz, 2H), 7.54 (d, j) 4.5 Hz, 2H), 7.31 (m, 2H), 6.81 (d, J=7.7 Hz, 2H), 6.69 (m, 2H). $^{13}$C NMR (CDCl$_3$, 126 MHz, 25° C.): δ 156.0, 145.3, 145.2, 136.3, 130.3, 128.3, 120.0, 113.6, 112.4. Anal. calculated for C$_{18}$H$_{12}$N$_3$Li: C, 77.98; H, 4.36; N, 15.16. Found: C, 77.92; H, 4.41; N, 14.39.

Example 6

Synthesis of [T1][BQA] (6)

[Li][BQA] (500 mg, 1.803 mmol) and thallium triflate (637 mg, 1.803 mmol) were dissolved separately in THF (25 mL) and cooled to −30° C. The thallium triflate was then added to the [Li][BQA] quickly, and the solution was stirred for 48 h at RT. THF was removed in vacuo, and the resulting red residue was extracted with benzene, filtered through Celite, and dried by benzene lyophilization to afford a red powder. The crude product was washed with petroleum ether (5×30 mL) and dried to afford 6 (454 mg, 53%). The product contained trace impurities of LiOTf, the complete removal of which has thus far proved problematic. $^1$H and $^{13}$C NMR, in addition to an X-ray diffraction study of a single crystal obtained by vapor diffusion of petroleum ether into a benzene solution, all support the assignment of the thallium complex 6.

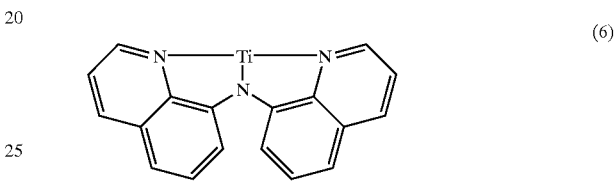

(6)

$^1$H NMR (C$_6$D$_6$, 300 MHz, 25° C.): δ 8.09 (br s, 2H), 7.72 (d, J=7.5 Hz, 2H), 7.51 (d, J=8.4 Hz, 2H), 7.29 (m, 2H), 6.81 (d, J=7.8 Hz, 2H), 6.70 br s, 2H). $^{13}$C NMR (C$_6$D$_6$, 75 MHz, 25° C.): δ 154.9, 145.7, 144.6, 137.8, 132.5, 127.9, 121.0, 114.9, 114.1.

Example 7

Synthesis of (BQA)PtCl (7)

A benzene solution (20 mL) of [Li][BQA] (370.5 mg, 1.336 mmol) was quickly added to a flask containing (COD)PtCl$_2$ (500 mg, 1.336 mmol) dissolved in benzene (30 mL) that had been chilled to −35° C. The stirring reaction solution was allowed to warm slowly and was subsequently heated at 65° C. for an additional 20 h. The resulting intense purple solution was filtered through Celite, followed by additional washings with DCM (3×10 mL). Solvent was removed from the filtrate in vacuo. The resulting purple solid was washed with petroleum ether (3×30 mL) and dried, affording a purple powder (454 mg, 68%). This powder was easily recrystallized in a hexane/chloroform diffusion chamber.

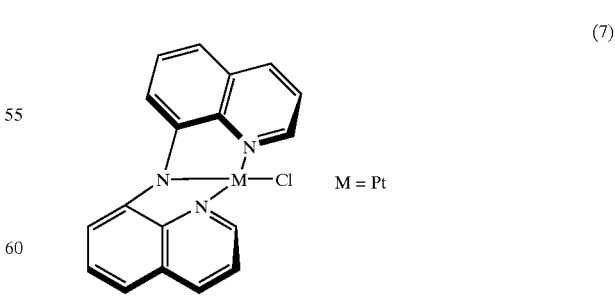

(7)

$^1$H NMR (CDCl$_3$, 300 MHz, 25° C.): δ 9.14 (d, J=5.0 Hz, 2H, $^3$J$_{PtH}$) 37 Hz), 8.23 (d, J=8.3 Hz, 2H), 7.62 (d, J=8.0 Hz, 2H), 7.43 (m, 2H), 7.37 (m, 2H), 7.02 (d, J=8.4 Hz, 2H). $^{13}$C NMR (CDCl$_3$, 75 MHz, 25° C.): δ 148.8, 148.7, 148.4, 138.9, 131.4, 129.4, 121.2, 115.7, 113.6. LR-MS (electrospray): calculated for $C_{18}H_{12}ClN_3Pt$ (M)$^+$ m/z 500. found (M+H)$^+$ m/z 501. Anal. Calcd for $C_{18}H_{12}ClN_3Pt$: C, 43.17; H, 2.42; N, 8.39. Found: C, 42.81; H, 2.47; N, 8.03.

Example 8

Alternative Synthesis of (7)

To a reaction vessel containing 1 (1.00 g, 3.6 mmol) and (COD)PtCl$_2$ (1.346 g, 3.6 mmol) dissolved in THF (30 mL), Et$_3$N (651 μL, 4.68 mmol) was added in one portion. The vessel was sealed and stirred at 95° C. for 48 h. The resulting red solution was cooled and dried in vacuo, extracted with CH$_2$Cl$_2$ (50 mL), and filtered through Celite on a sintered-glass frit. The solvent was again removed under reduced pressure, and the precipitate was washed with methanol (3×30 mL) and petroleum ether (2×10 mL) and then dried in vacuo to give the desired product (1.176 g, 65%). Spectral data were consistent with those reported above.

Example 9

Synthesis of (BQA)PdCl (8)

To a reaction flask containing (COD)PdCl$_2$ (1.05 g, 3.6 mmol) dissolved in THF (75 mL) was added a THF solution of 1 (1.00 g, 3.6 mmol) and Et$_3$N (651 μL, 4.68 mmol). The vessel was sealed and heated at 95° C. for 48 h. After the reaction was cooled, the reaction solution volatiles were removed in vacuo, affording a red residue. This crude product was dissolved in CH$_2$Cl$_2$ (50 mL), filtered through Celite on a sintered-glass frit, and washed with dilute brine solution (3×20 mL). The volume was reduced in vacuo, and the product was precipitated from solution with hexanes. The resulting red microcrystalline solid was washed with petroleum ether (3×15 mL) and dried to afford spectroscopically pure product 8 (915 mg, 62%). An analytically pure sample was obtained from a hexanes/chloroform diffusion chamber.

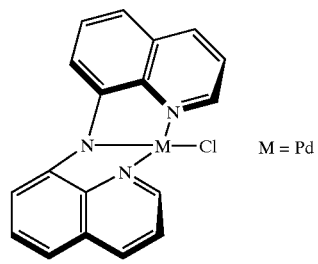

(8) M = Pd $^1$H NMR (CDCl$_3$, 300 MHz, 25° C.): δ 8.95 (d, J=5 Hz, 2H), 8.20 (d, J=8.2 Hz, 2H), 7.65 (d, J=8.2 Hz, 2H), 7.46 (m, 2H), 7.37 (m, 2H), 7.07 (d, J=8.2 Hz, 2H). $^{13}$C NMR (CDCl$_3$, 75 MHz, 25° C.): δ 149.5, 148.9, 148.3, 138.8, 131.2, 129.5, 121.3, 115.1, 112.6. LR-MS (electrospray): calculated for $C_{18}H_{12}ClN_3Pd$ (M)$^+$ m/z 411. found (M–Cl)$^+$ m/z 376. Anal. Calcd for $C_{18}H_{12}N_3PdCl$: C, 52.45; H, 2.93; N, 10.19. Found: C, 52.17; H, 2.92; N, 9.80.

Example 10

Alternative Synthesis of (8)

A solution of 5 (0.100 g, 0.361 mmol) in DCM (5 mL) was added dropwise to a stirring solution of (COD)PdCl$_2$ (0.103 g, 0.361 mmol) in DCM (10 mL). The solution became red-brown immediately upon addition. The reaction solution was stirred at 62° C. for 24 h, after which time it was cooled and dried in vacuo. The red solid was washed successively with EtOH (3×10 mL), Et$_2$O (2×10 mL), and pentane (2×10 mL) and then dried thoroughly under reduced pressure to yield a red solid (114 mg, 77%). Spectral data were analogous with those reported above.

Example 11

Synthesis of (BQA)NiCl (9)

A 200 mL reaction bomb was charged with 5 (200 mg, 0.722 mmol) dissolved in THF (50 mL). A slurry of (DME)NiCl$_2$ in THF (10 mL) was added to the stirring purple solution. The solution began to turn red immediately upon addition. The vessel was sealed with a Teflon stopcock and heated at 62° C. for 20 h. The reaction solution was allowed to cool, and the solvent was removed in vacuo. The resulting red solid was washed with Et$_2$O (50 mL), and LiCl was removed by extraction with EtOH (4×30 mL) followed by Et$_2$O (2×10 mL). The product was dried for 24 h under reduced pressure to yield a microcrystalline red solid (220 mg, 84%). Complex 9 may be recrystallized from a hexanes/chloroform diffusion chamber.

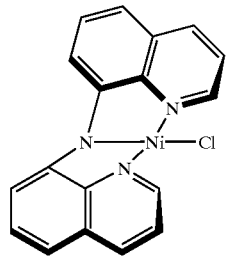

(9)

$^1$H NMR (CDCl$_3$, 300 MHz, 25° C.): δ 8.66 (d, J=5 Hz, 2H), 8.13 (d, J=8 Hz, 2H), 7.49 (d, J=8 Hz, 2H), 7.40 (m, 2H), 7.27 (m, 2H), 6.95 (d, J=8 Hz, 2H). $^{13}$C NMR (CDCl$_3$, 75 MHz, 25° C.): δ 150.6, 148.0, 147.8, 138.7, 129.8, 129.5, 121.3, 114.0, 111.7. LR-MS (electrospray): calculated for $C_{18}H_{12}ClN_3Ni$ (M)$^+$ m/z 363. found (M–Cl)$^+$ m/z 328. Anal. calculated for $C_{18}H_{12}N_3ClNi$: C, 59.32; H, 3.32; N, 11.53. Found: C, 59.19; H, 3.31; N, 11.33.

Example 12

Alternative Synthesis of (9)

Ligand 1 (0.123 g, 0.455 mmol) and (DME)NiCl$_2$ (0.100 g, 0.455 mmol) were dissolved in THF (10 mL) at RT. An aliquot of Et$_3$N (190 1L, 1.365 mmol) was added in one portion. Within several minutes, the reaction solution became red. Stirring was continued at 62° C. for 24 h. The resulting red solution was cooled and dried in vacuo. The solid product was then washed successively with EtOH (3×10 mL), Et$_2$O (2×10 mL), and pentane (2×10 mL) and dried under reduced pressure for 24 h to yield 9 (147 mg, 89%). Spectral data were consistent with those reported above.

Example 13

Synthesis of (o-(NMe$_2$)Ph-QAH)Pt(1,2-η$^2$-6-σ-cycloocta-1,4-dienyl) (10)

A 2 mL CH$_2$Cl$_2$ solution of (0.0706 g, 0.268 mmol) and NEt$_3$ (0.0814 g, 0.804 mmol) was added dropwise to a stirring solution of (COD)PtCl$_2$ (0.100 g, 0.268 mmol) in 3 mL of CH$_2$Cl$_2$. The reaction gradually turned red in color and was allowed to stir for 24 h at RT, after which time the volatiles were removed in vacuo. The resulting crude red solid was then dissolved in 5 mL of benzene, filtered, and lyophilized. Trituration with petroleum ether (3×3 mL) followed by drying in vacuo yielded the analytically pure product (0.148 g, 98%) as a mixture of two spectroscopically observable isomers in a 3:1 ratio (vide infra). X-ray quality crystals were grown by vapor diffusion of petroleum ether into a benzene solution of 10. The compound was produced as two spectroscopically distinct isomers 10a and 10b.

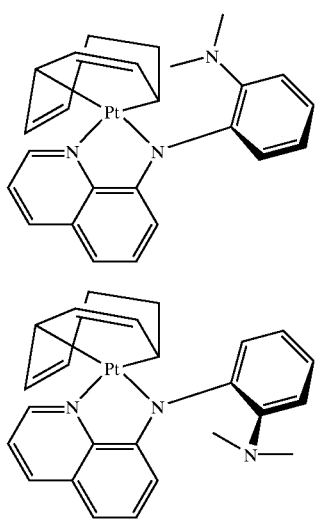

Because of overlapping resonances resulting from the two isomers, it was not possible to reliably integrate the $^1$H NMR spectrum. The observed resonances for the $^1$H and $^{13}$C NMR are reported.

$^1$H NMR (CDCl$_3$, 300 MHz, 25° C.): δ 8.20 (dd, J=1.0, 8.0 Hz), 8.04 (dd, J=1.0, 4.8 Hz, $^3$J$_{PtH}$) 17 Hz), 6.93–7.45 (m), 6.76 (m), 6.31 (m), 5.53 (m), 5.34 (m), 4.93 (m, $^2$J$_{PtH}$) 72 Hz), 4.62 (m, $^2$J$_{PtH}$) 72 Hz), 3.57 (m), 3.00–3.2 (m), 2.77 (m, NMe$_2$, major isomer), 2.72 (m, NMe$_2$, minor isomer), 1.20–2.0 (m). $^{13}$C NMR (CDCl$_3$, 75 MHz, 25° C.): δ 156.9, 149.3, 141.9, 142.2, 141.7, 138.0, 135.8, 135.4, 133.9, 130.5, 130.4, 130.3, 130.2, 129.4, 129.0, 128.3, 126.8, 125.2, 121.5, 121.2, 121.0, 120.9, 118.2, 117.4, 110.7, 110.6, 109.9, 76.7, 71.0, 53.3, 46.4, 43.7, 42.8, 40.9, 40.4, 40.2, 36.4, 33.7, 31.7, 28.9, 28.7, 28.3, 27.0, 25.6, 25.0, 24.9, 9.29, 8.50. LR-MS (electrospray): calculated for C$_{25}$H$_{27}$N$_3$Pt (M)$^+$ m/z 564. found (M+H)$^+$ m/z 565. Anal. calculated for C$_{25}$H$_{27}$N$_3$Pt: C, 53.18; H, 4.82; N, 7.44. Found: C, 53.45; H, 4.75; N, 7.19.

Example 14

Synthesis of (3,5-Me$_2$Ph-QA)Pt(1,2-η$^2$-6-σ-cycloocta-1,4-dienyl) (11)

A 2 mL CH$_2$Cl$_2$ solution of 4 (0.0666 g, 0.268 mmol) and NEt$_3$ (0.0814 g, 0.804 mmol) was added dropwise to a stirring solution of (COD)PtCl$_2$ (0.100 g, 0.268 mmol) in 3 mL of CH$_2$Cl$_2$. The reaction gradually turned red in color and was allowed to stir for 24 h at RT, after which time the volatiles were removed in vacuo. The resulting crude red solid was then dissolved in 5 mL of benzene, filtered, and lyophilized. Trituration with petroleum ether (3×3 mL) followed by drying in vacuo yielded a spectroscopically pure product (0.140 g, 95%). X-ray quality crystals were grown from vapor diffusion of petroleum ether into benzene.

$^1$H NMR (CDCl$_3$, 300 MHz, 25° C.): δ 8.20 (dd, J=1.0, 8.4 Hz, 1H), 8.05 (dd, J=1.0, 4.5 Hz, 1H, $^3$J$_{PtH}$) 17 Hz), 7.41 (m, 1H), 7.25 (m, 1H), 6.87 (s, 2H), 6.83 (s, 1H), 6.77 (d, J=8.1 Hz, 1H), 6.60 (d, J=8.1 Hz, 1H), 5.54 (m, 1H), 5.36 (m, 1H), 4.97 (m, 1H, $^2$J$_{PtH}$) 72 Hz), 4.65 (m, 1H, $^2$J$_{PtH}$) 72 Hz), 3.16 (m, 1H), 2.80 (m, 1H), 2.35 (s, 6H), 2.00–1.32 (m, 5H). $^{13}$C NMR (CDCl$_3$, 75 MHz, 25° C.): δ 159.1, 150.4, 142.1, 138.5, 138.0, 135.5, 131.2, 130.4, 129.0, 128.5, 125.9, 125.7, 121.2, 111.1, 109.5, 77.2, 70.7, 41.0, 31.5, 28.8, 24.9, 21.8. LR-MS (electrospray): calculated for C$_{25}$H$_{26}$N$_2$Pt (M)$^+$ m/z 549. found (M+H)$^+$ m/z 550. Anal. calculated for C$_{25}$H$_{26}$N$_2$Pt: C, 54.64; H, 4.77; N, 5.10. Found: C, 54.61; H, 5.01; N, 4.99.

Example 15

X-Ray Crystal Structure Analysis of [Li][FBQA] (5)

X-ray quality crystals were obtained from a benzene/petroleum ether diffusion chamber at 25° C. A red crystalline blade was mounted on a glass fiber with Paratone-N oil (an Exxon product). The structure was solved by direct methods in conjunction with standard difference Fourier techniques. The largest peak and hole in the difference map were 0.351 and −0.195 e Å$^{-3}$, respectively. Maximum and minimum transmissions were equal to 0.9971 and 0.9684, respectively. Crystal data for C$_{36}$H$_{24}$—Li$_2$N$_6$: monoclinic space group P2$_1$/c (No. 14), a=22.490(3) Å, b=8.6035(10) Å, c=14.4810 (17) Å, β=97.875(2)°, V=2775.5(6) Å$^3$, Z=4, D$_{calcd}$=1.327 g cm$^{-3}$, abs coefficient=0.079 mm$^{-1}$, λ(Mo Kα)=0.710 73 Å, T=98(2) K, Bruker SMART 1000 CCD, crystal size=0.41× 0.3×0.04 mm$^3$, θ$_{max}$=28.36°, R1=0.0525, wR2=0.0835, for I>2σ(I) R1=0.1141, wR2=0.0877, number of reflections collected=39470 (−29≤h≤29, −11≤k≤11, −19≤l≤18), number of independent reflections=6569, number of parameters=493.

Example 16

X-Ray Crystal Structure Analysis of [Tl][BQA] (6)

X-ray quality crystals were obtained from a benzene/petroleum ether diffusion chamber at 25° C. A red crystalline blade was mounted on a glass fiber with Paratone-N oil. The structure was solved by direct methods in conjunction with standard difference Fourier techniques. The largest peak and hole in the difference map were 1.738 and −1.191 e Å$^{-3}$, respectively. SADABS data correction was applied on the basis of pseudo-ψ scans with maximum and minimum transmissions equal to 0.7535 and 0.7213, respectively. Crystal data for C$_{18}$H$_{12}$N$_3$Tl: ortho-rhombic space group Pna2$_1$ (No. 33), a=6.9767(11) Å, b=23.289(4) Å, c=8.7724 (13) Å, V=1425.3(4) Å$^3$, Z=4, D$_{calcd}$=2.212 g cm$^{-3}$, abs coefficient=11.330 mm$^{-1}$, λ(Mo Kα)=0.710 73 Å, T=98(2) K, Bruker SMART 1000 CCD, crystal size 0.89×0.23×0.16 mm$^3$, θ$_{max}$=28.3°, R1=0.0245, wR2=0.0397, for I>2σ(I) R1=0.0336, wR2=0.0405, number of reflections collected= 22995 (−9≤h≤8, −29≤k≤30, −11≤l≤11), number of independent reflections=3324, number of parameters=199.

Example 17

X-Ray Crystal Structure Analysis of (BQA)PtCl (7)

X-ray quality crystals were obtained from a chloroform/petroleum ether diffusion chamber at 25° C. A dark red crystalline column was mounted on a glass fiber with Paratone-N oil. The structure was solved by direct methods in conjunction with standard difference Fourier techniques. The largest peak and hole in the difference map were 1.015 and −0.976 e Å$^{-3}$, respectively. SADABS data correction was applied on the basis of pseudo-ψ scans with maximum and minimum transmissions equal to 1.0000 and 0.5322, respectively. Crystal data for $C_{18}H_{12}ClN_3Pt$: monoclinic space group P2$_1$/n (No. 14), a=9.1532(12) Å, b=11.5481(15) Å, c=15.1060(19) Å, β8=106.997(2)°, V=1527.0(3) Å$^3$, Z=4, $D_{calcd}$=2.179 g cm$^{-3}$, abs coefficient=9.365 mm$^{-1}$, λ(Mo Kα)=0.71073 Å, T=98(2) K, Bruker SMART 1000 CCD, crystal size=0.28×0.22×0.22 mm$^3$, $θ_{max}$28.1°, R1=0.0245, wR2=0.0452, for I>2σ(I) R1=0.0331, wR2= 0.0460, number of reflections collected=26365 (−11≦h≦12, −14≦k≦15, −19≦l≦19), number of independent reflections=3635, number of parameters=256.

Example 18

X-Ray Crystal Structure Analysis of (BQA)PdCl (8)

X-ray quality crystals were obtained from a chloroform/petroleum ether diffusion chamber at 25° C. A dark red crystalline column was mounted on a glass fiber with Paratone-N oil. The structure was solved by direct methods in conjunction with standard difference Fourier techniques. The largest peak and hole in the difference map were 0.587 and −0.522 e Å$^{-3}$, respectively. No data correction was applied. Maximum and minimum transmissions were equal to 0.7428 and 0.6828, respectively. Crystal data for $C_{18}H_{12}ClN_3Pd$: monoclinic space group P2$_1$/n (No. 14), a=7.5343(7) Å, b=14.9983(14) Å, c=12.8184(12) Å, β=93.845(2)°, V=1445.2(2) Å$^3$, Z=4, $D_{calcd}$=1.894 g cm$^{-3}$, abs coefficient=1.470 nm$^{-1}$, λ(Mo Kα)=0.71073 Å, T=98(2) K, Bruker SMART 1000 CCD, crystal size=0.28×0.22×0.22 mm$^3$, $θ_{max}$=28.0°, R1=0.0267, wR2=0.0544, for I>2σ(I) R1=0.0318, wR2=0.0549, number of reflections collected= 20400 (−9≦h≦9, −18≦k≦19, −16≦l≦16), number of independent reflections=3343, number of parameters=256.

Example 19

X-Ray Crystal Structure Analysis of (BQA)NiCl (9)

X-ray quality crystals were obtained from a chloroform/hexanes diffusion chamber at 25° C. A dark red crystalline block was mounted on a glass fiber with Paratone-N oil. The structure was solved by direct methods in conjunction with standard difference Fourier techniques. The largest peak and hole in the difference map were 0.309 and −0.377 e Å$^{-3}$, respectively. Maximum and minimum transmissions were equal to 0.7535 and 0.7213, respectively. Crystal data for $C_{18}H_{12}ClN_3Ni$: monoclinic space group P2$_1$/n (No. 14), a=8.9635(7) Å, b=11.4785(9) Å, c=14.9909(12) Å, β=107.3220(10)°, V=1472.4(2) Å$^3$, Z=4, $D_{calcd}$=1.644 g cm$^{-3}$, abs coefficient=1.500 mm$^{-1}$, λ(Mo Kα)=0.71073 Å, T=98(2) K, Bruker SMART 1000 CCD, crystal size=0.23× 0.20×0.20 mm$^3$, $θ_{max}$=28.2°, R1=0.0317, wR2=0.0615, for I>2σ(I) R1=0.0426, wR2=0.0627, number of reflections collected=20863 (−11≦h≦11, −15≦k≦14, −19≦l≦19), number of independent reflections=3452, number of parameters=256.

Example 20

X-Ray Crystal Structure Analysis of (o-(NMe$_2$)Ph-QAH)Pt(1,2-η$^2$-6-σ-cycloocta-1,4-dienyl) (10a)

X-ray quality crystals were obtained from a benzene/petroleum ether diffusion chamber at 25° C. A red crystalline block was mounted on a glass fiber with Paratone-N oil. The structure was solved by direct methods in conjunction with standard difference Fourier techniques. The largest peak and hole in the difference map were 1.488 and −0.577 e Å$^{-3}$, respectively. Maximum and minimum transmissions were equal to 1.0000 and 0.7282, respectively. Crystal data for $C_{25}H_{27}N_3Pt$: triclinic space group P1 (No. 2), a=7.5521(7) Å, b=10.7997(9) Å, c=13.4693(12) Å, α=108.3110(10)°, β=107.3220(10)°, γ=94.7070(10)°, V=1034.23(16) Å$^3$, Z=2, $D_{calcd}$=1.813 g cm$^{-3}$, abs coefficient=6.800 mm$^{-1}$, λ(Mo Kα)=0.71073 Å, T=98(2) K, Bruker SMART 1000CCD, crystal size=0.22×0.19×0.15 mm$^{-3}$, $θ_{max}$=28.31°, R1=0.0237, wR2=0.0413, for I>2σ(I) R1=0.0204, wR=2= 0.0410, number of reflections collected=15396 (−9≦h≦10, −14≦k≦14, −17≦l≦17), number of independent reflections=4745, number of parameters=370.

Example 21

X-Ray Crystal Structure Analysis of (3,5-Me$_2$Ph-QA)Pt(12-η$^2$-6-σ-cycloocta-1,4-dienyl) (11)

X-ray quality crystals were obtained from a benzene/petroleum ether diffusion chamber at 25° C. A red crystalline block was mounted on a glass fiber with Paratone-N oil. The structure was solved by direct methods in conjunction with standard difference Fourier techniques. The largest peak and hole in the difference map were 1.357 and −0.496 e Å$^{-3}$, respectively. Maximum and minimum transmissions were equal to 1.0000 and 0.6946, respectively. Crystal data for $C_{25}H_{26}N_2Pt$: orthorhombic space group P2$_1$2$_1$2$_1$, a=9.2884 (7) Å, b=11.4127(9) Å, c=19.3116(12) Å, V=2047.1(3) Å$^3$, Z=4, $D_{calcd}$=1.783 g cm$^{-3}$, abs coefficient=6.867 mm$^{-1}$, λ(Mo Kα)=0.71073 Å, T=98(2) K, Bruker SMART 1000 CCD, crystal size=0.29×0.13×0.07 mm$^3$, $θ_{max}$28.4°, R1=0.0210, wR2=0.0347, for I>2σ(I) R1=0.0192, wR2= 0.0344, number of reflections collected=30635 (−12≦h≦12, −14≦k≦15, −25≦l≦25), number of independent reflections=4878, number of parameters=335.

We claim:

1. A tri- or bidentate amido ligand having the formula:

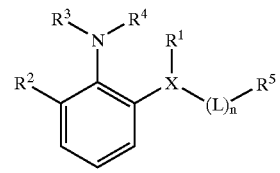

wherein:

R$^1$ is selected from the group consisting of hydrogen, hydrocarbyl, substituted hydrocarbyl, heteroatom-containing hydrocarbyl and substituted heteroatom-containing hydrocarbyl;

X is selected from the group consisting of N and P;

L is hydrocarbylene;

n is 0 or 1;

R$^5$ is selected from the group consisting of naphtahyl, pyridinyl, or quinolyl, which are optionally substituted with one or more alkyl, substituted alkyl, alkoxy, alkylsulfonyl, and amino moities; and R$^2$, R$^3$, and R$^4$ are independently selected from hydrogen and hydrocarbyl, or wherein R$^2$ and R$^3$ may be taken together to form a 5- or 6-membered ring structure selected from the group consisting of cycloalkyl, substituted cycloalkyl, aryl, substituted aryl, heteroaryl, and substituted heteroaryl, and wherein $R^4$ may be absent when $R^2$ and $R^3$ are taken together to form the 5- or 6-membered ring structure;

with the proviso that when $R^2$ and $R^3$ are taken together to form a 6-membered unsubstituted aryl ring, $R^1$ and $R^4$ are H, and n is 0, then $R^5$ may not be a quinoline moiety connected at the $C_8$ position or an unsubstituted napthalene moiety when X is also N.

2. The compound of claim 1 wherein $R^2$ and $R^3$ are taken together to form a 5- or 6-membered aryl, substituted aryl, heteroaryl, or substituted heteroaryl.

3. The compound of claim 1 wherein $R^2$ and $R^3$ are taken together to form a 6-membered heteroaryl or substituted heteroaryl.

4. The compound of claim 1 wherein $R^1$ is selected from the group consisting of hydrogen, hydrocarbyl, and substituted hydrocarbyl.

5. The compound of claim 4 wherein $R^1$ is selected from the group consisting of hydrogen and alkyl.

6. The compound of claim 1 wherein $R^4$ is selected from the group consisting of hydrogen and alkyl.

7. The compound of claim 1 wherein n is 0.

8. The compound of claim 1 wherein n is 1 and L is a $C_{1-12}$ alkylene.

9. The compound of claim 1 wherein X is N.

10. The compound of claim 1 wherein X is P.

11. The compound of claim 1 having the formula:

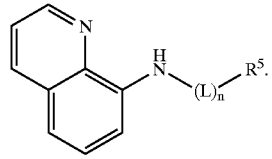

12. A method for synthesizing the tri- or bidentate amino ligand of claim reacting:
 (a) an amino-substituted, N-heteroaryl compound; and
 (b) a halogen-substituted aromatic compound;
 in the presence of a transition metal catalyst.

13. The method of claim 12 wherein the transition metal catalyst comprises a metal atom and at least one chelating ligand.

14. The method of claim 13 wherein the metal atom is selected from the group consisting of iron, ruthenium, osmium, cobalt, rhodium, iridium, nickel, palladium and platinum.

15. The method of claim 14 wherein the metal atom is selected from the group consisting of nickel, palladium, and platinum.

16. The method of claim 15 wherein the metal atom is $Pd^0$.

17. The method of claim 13 wherein the chelating ligand comprises at least one atom selected from the group consisting of nitrogen, phosphorus, arsenic, antimony, and bismuth.

18. The method of claim 17 wherein the atom is selected from the group consisting of nitrogen, phosphorus, and arsenic.

19. The method of claim 18 wherein the atom is selected from the group consisting of nitrogen and phosphorus.

20. The method of claim 17 wherein the chelating ligand comprises one metal atom, and further comprises a chelating element selected from the group consisting of oxygen and sulfur.

21. The method of claim 20 wherein the chelating ligand is an arylene or metallocene substituted with at least one of said metal atoms.

22. The method of claim 21 wherein the arylene is a $C_{4-20}$ arylene.

23. The method of claim 22 wherein the $C_{4-20}$ arylene is a binaphthyl compound.

24. The method of claim 21 wherein the metallocene is ferrocene.

25. The method of claim 21 wherein the chelating ligand is bidentate and the metal atom is phosphorous.

26. The method of claim 9 wherein the transition metal catalyst is prepared in situ.

27. The method of claim 9 wherein the amino-substituted, N-heteroaryl compound has the formula:

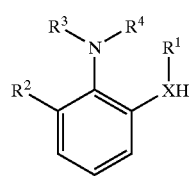

wherein:

$R^1$ is selected from the group consisting of hydrogen, hydrocarbyl, substituted hydrocarbyl, heteroatom-containing hydrocarbyl and substituted heteroatom-containing hydrocarbyl;

X is selected from the group consisting of N and P; and $R^2$, $R^3$, and $R^4$ are independently selected from hydrogen and hydrocarbyl, or wherein $R^2$ and $R^3$ may be taken together to form a 5- or 6-membered ring structure selected from the group consisting of cycloalkyl, substituted cycloalkyl, aryl, substituted aryl, heteroaryl, and substituted heteroaryl, and wherein $R^4$ may be absent when $R^2$ and $R^3$ are taken together to form the 5- or 6-membered ring structure.

28. The compound of claim 27 wherein $R^2$ and $R^3$ are taken together to form a 5- or 6-membered aryl, substituted aryl, heteroaryl, or substituted heteroaryl.

29. The compound of claim 28 wherein $R^2$ and $R^3$ are taken together to form a 6-membered heteroaryl or substituted heteroaryl.

30. The compound of claim 27 wherein $R^4$ is selected from the group consisting of hydrogen and alkyl.

31. The method of claim 9 wherein the halogen substituted aromatic compound has the formula:

$$Z\text{---}(L)_n\text{---}R^5$$

wherein:

Z is halo;

L is hydrocarbylene;

n is 0 or 1; and $R^5$ is selected from the group consisting of naphthyl, pyridinyl, or quinolyl which are optionally substituted with one or more alkyl, substituted alkyl, alkoxy, alkylsulfanyl, and amino moieties.

* * * * *